United States Patent
Goerlach-Doht et al.

(10) Patent No.: US 9,352,330 B2
(45) Date of Patent: May 31, 2016

(54) PROCESS FOR PRODUCING CELLULOSE DERIVATIVES OF HIGH BULK DENSITY AND GOOD FLOWABILITY

(75) Inventors: Yvonne M. Goerlach-Doht, Rosengarten (DE); Juergen Hermanns, Nottensdorf (DE); Marco Grossstueck, Walsrode (DE)

(73) Assignee: Dow Global Technologies LLC

(*) Notice: Subject to any disclaimer, the term of this patent is extended or adjusted under 35 U.S.C. 154(b) by 263 days.

(21) Appl. No.: 14/009,432

(22) PCT Filed: Mar. 29, 2012

(86) PCT No.: PCT/US2012/031111
§ 371 (c)(1),
(2), (4) Date: Oct. 2, 2013

(87) PCT Pub. No.: WO2012/138532
PCT Pub. Date: Oct. 11, 2012

(65) Prior Publication Data
US 2014/0017319 A1    Jan. 16, 2014

Related U.S. Application Data

(60) Provisional application No. 61/472,225, filed on Apr. 6, 2011.

(51) Int. Cl.
*B02C 23/00* (2006.01)
*B02C 23/18* (2006.01)
(Continued)

(52) U.S. Cl.
CPC ............. *B02C 23/18* (2013.01); *A61K 9/146* (2013.01); *B02C 23/24* (2013.01); *C08B 11/20* (2013.01);
(Continued)

(58) Field of Classification Search
CPC .......... B02C 23/00; B02C 23/18; B02C 23/24
USPC ................... 241/23, 17–18, 27, 57
See application file for complete search history.

(56) References Cited

U.S. PATENT DOCUMENTS

| 4,734,285 A | 3/1988 | Alderman |
| 4,979,681 A | 12/1990 | Donges et al. |

(Continued)

FOREIGN PATENT DOCUMENTS

| EP | 0370447 | 5/1990 |
| EP | 0384046 A1 | 8/1990 |

(Continued)

OTHER PUBLICATIONS

Weinheim "Methoden der Org." 4the Ed. 1987, vol. E20, 2048-2076.
(Continued)

*Primary Examiner* — Faye Francis

(57) ABSTRACT

A particulate cellulose derivative is obtained in a process of grinding and drying a moist cellulose derivative wherein
A) a cellulose derivative having a moisture content of from 60 to 95 percent, based on the total weight of the moist cellulose derivative, is provided,
B) the moist cellulose derivative is dried and partially ground in a gas-swept impact mill; and
C) the ground and partially dried cellulose derivative is contacted with an additional amount of a drying gas outside the gas-swept impact mill.
The obtained particulate cellulose derivative has a high untapped bulk density and a good flowability.

11 Claims, 1 Drawing Sheet

(51) Int. Cl.
*B02C 23/24* (2006.01)
*C08B 11/20* (2006.01)
*C08J 3/12* (2006.01)
*C08L 1/28* (2006.01)
*A61K 9/14* (2006.01)

(52) U.S. Cl.
CPC ............... *C08J 3/124* (2013.01); *C08L 1/284* (2013.01); *B02C 23/00* (2013.01); *C08J 2301/28* (2013.01); *Y10T 428/2982* (2015.01)

(56) References Cited

U.S. PATENT DOCUMENTS

| | | | |
|---|---|---|---|
| 6,021,966 A * | 2/2000 | Doenges | B02C 13/08 241/189.1 |
| 6,320,043 B1 | 11/2001 | Weber et al. | |
| 6,509,461 B2 | 1/2003 | Schlesiger et al. | |
| 7,259,257 B2 | 8/2007 | Schlesiger et al. | |
| 7,578,458 B2 * | 8/2009 | Perplies | C08J 3/12 241/15 |
| 7,683,110 B2 | 3/2010 | Schlesiger et al. | |
| 8,973,853 B2 * | 3/2015 | Pierini | C08J 3/12 241/23 |
| 2001/0025101 A1 | 9/2001 | Schlesiger et al. | |
| 2001/0034441 A1 | 10/2001 | Schlesiger et al. | |
| 2008/0039621 A1 | 2/2008 | Maruyama et al. | |

FOREIGN PATENT DOCUMENTS

| | | |
|---|---|---|
| EP | 0824107 | 2/1998 |
| EP | 0954536 | 11/1999 |
| EP | 1127895 | 8/2001 |
| EP | 1127910 | 8/2001 |
| EP | 1903059 | 3/2008 |
| GB | 2262527 | 6/1993 |
| WO | 9600748 | 1/1996 |
| WO | 2008127794 | 10/2008 |

OTHER PUBLICATIONS

Ulmann's Encyclopedia of Industrial Chemistry, 5th, vol. A5, 461-488, 1986.
Witt et al, PARTEC 2007, Current Limits of Particle size.

* cited by examiner

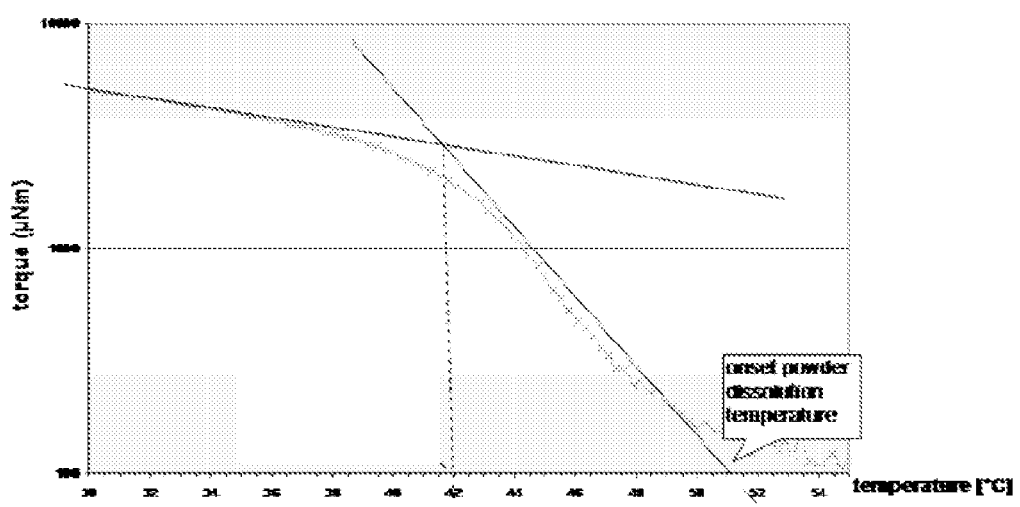

PROCESS FOR PRODUCING CELLULOSE DERIVATIVES OF HIGH BULK DENSITY AND GOOD FLOWABILITY

CROSS REFERENCE TO RELATED APPLICATIONS

This application is a 35 USC §371 national phase filing of PCT/US2012/031111, filed 29 Mar. 2012, which claims the benefit of Application No. 61/472,225, filed Apr. 6, 2011.

FIELD

The present invention relates to a process for producing a particulate cellulose derivative and to a particulate cellulose derivative of good flowability and optionally a high onset dissolution temperature.

BACKGROUND

Cellulose derivatives are industrially important and are used in a large variety of technology areas and in many different end-use applications, for example in the personal care or pharmaceutical industry, in agricultural applications, and in the building or oil industry. Their preparation, properties and applications are described, for example, in Ullmann's Encyclopedia of Industrial Chemistry, 5th Edition, (1986), Volume A5, pages 461-488, VCH Verlagsgesellschaft, Weinheim or in "Methoden der organischen Chemie" (methods of organic chemistry), 4th Edition (1987), Volume E20, Makromolekulare Stoffe, Part Volume 3, pages 2048-2076, Georg Thieme Verlag, Stuttgart.

Water-soluble cellulose derivatives have found widespread use. These water-soluble cellulose derivatives are conveniently supplied as a particulate dry material that is then dissolved in water for the desired end use of such water-soluble cellulose derivatives. Unfortunately, some water-soluble cellulose derivatives are difficult to dissolve in water due to the fact that the first particles that come into contact with water immediately swell and stick to each other, forming a gel-like barrier that shields the remaining particles from hydration. The above-described gel-blocking behavior of water-soluble cellulose derivatives is a considerable drawback for those applications of water-soluble cellulose derivatives that comprise the solution of the particulate water-soluble cellulose derivatives such as cellulose ethers in aqueous systems. The gel blocking behavior is visible as the formation of "lumps" which require a long time for complete dissolution. To overcome this gel blocking behavior or the formation of lumps the cellulose derivatives are dispersed in hot water, typically above about 80° C. During agitation the dispersion is cooled and dissolution of the cellulose derivative takes place. At a specific temperature the cellulose derivative starts to dissolve and to build up viscosity. Characteristic temperatures that describe the dissolution behavior are the onset dissolution temperature and the temperature at which the maximum of the dissolution rate is reached. This so-called hot/cold water dissolution technique takes advantage of the fact that water-soluble cellulose derivatives such as cellulose ethers are generally insoluble in hot water and soluble in cold water, depending on the type and degree of substitution. Unfortunately, this hot/cold water dissolution technique is quite time-consuming for those who have to prepare aqueous solutions of the cellulose derivatives. Providing water-soluble cellulose derivatives with a high onset dissolution temperature would be highly desirable since less cooling of the hot dispersions of the water-soluble cellulose derivative would be required to dissolve the cellulose derivative in water.

Another important use of cellulose derivatives, particularly water-soluble cellulose derivatives, is their incorporation as excipients in sustained release dosage forms. Sustained release dosage forms are designed to release a finite quantity of a compound into an aqueous environment over an extended period of time. Known sustained release pharmaceutical dosage forms contain a medicament or a vitamin whose rate of release is controlled by a polymeric matrix. Sustained release pharmaceutical dosage forms are desirable because they provide a method of delivering a long-lasting dose in a single application without overdosing. U.S. Pat. No. 4,734,285 discloses that the release of an active composition from a solid tablet can be prolonged by employing a fine particle sized hydroxypropyl methylcellulose ether composition as an excipient in the solid tablet. The particle size of the hydroxypropyl methylcellulose ether is so small that at least 90 percent by weight of the cellulose ether particles pass through a 100 mesh screen (149 micrometers mesh size), and preferably at least 97 percent by weight of the cellulose ether particles pass through a 140 mesh screen (105 micrometers mesh size) to achieve a long release profile. While such hydroxypropyl methylcellulose ether particles provide excellent release profiles to tablets, these particles of very small size are known to have poor flow properties. A poor flowability of the cellulose ether particles can lead to problems in the manufacturing of dosage forms such as tablets. Problems can include increased variability in tablet weight or tablet crushing strength from tablet-to-tablet as well as variation in the amount of active ingredient incorporated into each dosage form. Poor particle flow can also lead to consolidation of the powder bed in processing equipment, such as storage bins and tablet press feed hoppers.

The International Patent Application Publication No. WO 2008/127794 addresses the poor flowability of the hydroxypropyl methylcellulose ether disclosed in U.S. Pat. No. 4,734,285. WO 2008/127794 discloses a granular material having a mean particle diameter of 150 to 800 micrometers and an untapped bulk density of 0.1 to 0.35 g/cm$^3$, the main component of the granular material being a cellulose derivative. The granular material is a useful excipient for sustained-release dosage forms, particularly for excipients to be used in a direct compression process, due to the good flow and the good compactibility of the granular material leading to strong, hard tablets, with small variability in tablet-to-tablet physical properties, in combination with reproducible kinetics of the sustained release of the active ingredient. Unfortunately, it has been found that the low density of the granular material may cause some problems when blending the granular material with the active ingredient. Due to the low density of the granular material, the weight of the blend of granular material and active material in the blender typically has to be reduced to avoid overfilling of the blender, which reduces the throughput through the blender. Also, formulators may need to pre-compress the blend of granular material and active ingredient to be able to fill tablet dies with the target tablet weight.

Accordingly, it would be highly desirable to provide cellulose derivatives which have a good flowability in combination with a reasonably high untapped bulk density.

Accordingly, the object of the present invention is to find a way of increasing the flowability or the onset dissolution temperature of cellulose derivatives in particulate form. A preferred object of the present invention is to find a way of increasing the flowability and the onset dissolution temperature of cellulose derivatives in particulate form. Another preferred object of the present invention is to find a way of increasing the flowability and/or the onset dissolution temperature of cellulose derivatives in particulate form in such a manner that the particulate cellulose derivates have a reasonably high untapped bulk density.

Surprisingly, it has been found that the flowability and/or the onset dissolution temperature of cellulose derivatives in particulate form can be increased in a novel process for grinding and drying a moist cellulose derivative. Several processes for drying-grinding moist cellulose derivatives are known in the art, such as described in the patent applications GB 2 262 527 A; EP 0 824 107 A2; EP-B 0 370 447 (equivalent to U.S. Pat. No. 4,979,681); WO 96/00748 A1; EP 1 127 895 A1 (equivalent to US 2001/034441) and EP 0 954 536 A1 (equivalent to U.S. Pat. No. 6,320,043), but none of these references addresses the problem of increasing the onset dissolution temperature of cellulose derivatives in particulate form or provide an evidence of good flowability of the cellulose derivatives.

SUMMARY

One aspect of the present invention is a process for producing a particulate cellulose derivative by grinding and drying a moist cellulose derivative, which process comprises the steps of A) providing a cellulose derivative having a moisture content of from 60 to 95 percent, based on the total weight of the moist cellulose derivative, B) grinding and partially drying the moist cellulose derivative in a gas-swept impact mill; and C) contacting the ground and partially dried cellulose derivative with an additional amount of a drying gas outside the impact mill.

Another aspect of the present invention is a method of increasing the flowability and/or the onset dissolution temperature of a particulate cellulose derivative, which method comprises the steps of A) providing a cellulose derivative having a moisture content of from 60 to 95 percent, based on the total weight of the moist cellulose derivative, B) grinding and partially drying the moist cellulose derivative in a gas-swept impact mill; and C) contacting the ground and partially dried cellulose derivative with an additional amount of a drying gas outside the gas-swept impact mill.

Yet another aspect of the present invention is a particulate cellulose derivative having a median Equivalent Projected Circle Diameter (EQPC) of less than 140 micrometers, an untapped bulk density of at least 0.40 g/cm$^3$ and a Carr Index of 30 or less.

Yet another aspect of the present invention is a dosage form produced from a) one or more cellulose derivatives of the present invention, b) one or more active ingredients, and c) one or more optional adjuvants.

It has been surprisingly found that the flowability and/or the onset dissolution temperature of cellulose derivatives can be improved if a moist cellulose derivative is dried and ground in a gas-swept impact mill that has a moisture content of from 60 to 95 percent, based on the total weight of the moist cellulose derivative, and if the drying-grinding in the gas-swept impact mill is conducted in such a manner that the cellulose derivative is only partially dried in the gas-swept impact mill and the drying is completed in a gas drying step outside the impact mill.

BRIEF DESCRIPTION OF DRAWINGS

FIG. 1 illustrates how to measure the onset dissolution temperature of a particulate cellulose derivative.

DETAILED DESCRIPTION

The present invention relates to a process for producing a particulate cellulose derivative by drying and grinding a moist cellulose derivative.

The cellulose derivatives used in this process are generally soluble or at least soakable in solvents, preferably water. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the celluloses according to the invention are not limited to these groups.

Examples of cellulose derivatives are hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CMSEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC).

Preferred cellulose derivatives are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. Particularly preferred cellulose derivatives are cellulose ethers having a thermal flocculation point in water, such as, for example, methyl cellulose, methyl hydroxyethyl cellulose, methyl hydroxypropyl cellulose and hydroxypropyl cellulose. The cellulose derivatives are preferably water-soluble, which means that they have a solubility in water of at least 1 gram, more preferably at least 2 grams, most preferably at least 5 grams in 100 grams of distilled water at 25° C. and 1 atmosphere.

Most preferably, the water-soluble cellulose ether is a methylcellulose with a methyl degree of substitution $DS_{methyl}$ of from 1.2 to 2.2, preferably from 1.5 to 2.0; or a hydroxypropyl methylcellulose with a $DS_{methyl}$ of from 0.9 to 2.2, preferably from 1.1 to 2.0, and an $MS_{hydroxypropyl}$ of from 0.02 to 2.0, preferably from 0.1 to 1.2; or a hydroxyethyl methylcellulose with a $DS_{methyl}$ of from 1.15 to 2.3, preferably from 1.15 to 2.2, and an $MS_{hydroxyethyl}$ of from 0.03 to 1.0, preferably from 0.05 to 0.9; or a hydroxyethyl cellulose with an $MS_{hydroxyethyl}$ of from 1.2 to 3.0, preferably from 1.45 to 2.2. The determination of the ether side groups, i.e. the $DS_{methyl}$, $MS_{hydroxyethyl}$ and $MS_{hydroxypropyl}$ can be effected as described by K. L. Ketterer, W. E. Kester, D. L. Wiederrich, and J. A. Grover, Determination of Alkoxyl Substitution in Cellulose Ethers by Zeisel-Gas Chromatographie, Analytical Chemistry, Vol. 51, No. 13, November 1979, 2172-76.

The viscosities of the water-soluble cellulose ethers can vary over a broad range. In one aspect of the present invention the viscosity of the cellulose ether is more than 150 mPa·s, preferably from 500 to 200,000 mPa·s, more preferably from 500 to 100,000 mPa·s, most preferably from 1000 to 80,000, particularly from 1000 to 60,000, determined in a 1.5 by weight aqueous solution at 20° C. in a Haake RS600 rheometer with a cone and plate Geometry (CP-60/2°) at 20° C. and at a shear rate of 2.55 s⁻1. In another aspect of the present invention the viscosity of the cellulose ether is from 1.2 to 200 mPa·s, preferably from 2 to 100 mPa·s, more preferably from 2.5 to 50 mPa·s, in particular from 3 to 30 mPa·s, measured as a 2 weight-% aqueous solution at 20° C. according to ASTM D2363-79 (Reapproved 2006). Such low viscosity cellulose ethers can be produced in a known manner by partial degradation of higher viscosity cellulose ethers.

The production of cellulose derivatives, preferably cellulose ethers and cellulose esters, is known in the art. Typically the production process involves activating the cellulose, for example by treatment with an alkali metal hydroxide, reacting the thus treated cellulose with a derivatizing agent, such as an etherifying or esterifying agent, and washing the cellulose derivative to remove by-products. After the washing step the cellulose derivative generally has a moisture content of from 30 to 60 percent, typically from 45 to 55 percent, based on the total weight of the moist cellulose derivative. While the preferred washing liquor may depend on the specific type of cellulose derivative, preferred washing liquors generally are water, isopropanol, acetone, methylethylketone or brine. More preferred washing liquors generally are water or brine. Cellulose derivatives are generally washed at a temperature of from 20 to 120° C., preferably from 65 to 95° C. A solvent-moist, preferably a water-moist filter cake is obtained after washing and separating the cellulose derivative from the washing liquor. The moist cellulose derivative is usually obtained in the shape of moist granules, moist lumps and/or a moist paste.

According to one aspect of the present invention the cellulose derivative has been obtained by separating a cellulose derivative from a suspension thereof in a liquid, such as water, and is subsequently subjected to the process of the present invention. The suspension of particles in a liquid can originate from the production and washing the cellulose derivative, as described above. Separating a cellulose derivative from a suspension can be carried out in a known way, such as centrifugation.

According to another aspect of the present invention a dry cellulose derivative and a liquid, such as water, can be mixed in a compounder to a desired moisture content and the thus obtained moist cellulose derivative is subsequently subjected to the process of the present invention. The compounder preferably allows thorough and intense mixing. Useful compounders are, for example, granulators, kneaders, extruders, presses, or roller mills, wherein the mixture of the cellulose derivative and liquid is homogenised by applying shear forces and compounding, such as a twin-screw compounder. Co-rotating as well as counter-rotating machines are suitable. So-called divided trough kneaders with two horizontally arranged agitator blades that engage deeply with one another and that perform a mutual stripping action, as in the case of twin-screw compounders are particularly suitable. Suitable single-shaft, continuous kneaders include the so-called Reflector® compounders, which are high performance mixers of modular construction, consisting of a multi-part, heatable and coolable mixing cylinder and a unilaterally mounted blade mixer (manufacturer: Lipp, Germany). Also suitable are so-called pinned cylinder extruders or Stiftconvert® extruders (manufacturer: Berstorff, Germany). The pins incorporated in the housing serve as abutments in order to prevent the kneaded material rotating together with the shaft. Kneader mixers with so-called double-blade sigma stirrers (manufacturer: Fima, Germany) in a horizontal assembly are particularly suitable. The blades operate at different speeds and their direction of rotation can be reversed. A stirred vessel with a vertically arranged mixer shaft is also suitable if suitable flow baffles are mounted on the vessel wall in order to prevent the kneaded mass rotating together with the stirrer shaft, and in this way an intensive mixing action is imparted to the kneaded material (manufacturer: Bayer AG). Also suitable are double-walled mixing vessels with a planetary stirrer and inline homogeniser.

In step A) of the process and method of the present invention a cellulose derivative is provided that has a moisture content of from 60 to 95 percent, based on the total weight of the moist polysaccharide derivative. Preferred lower limits of the moisture content are 65, 70 and 75 percent respectively. Preferred upper limits of the moisture content are 92, 90 and 85 percent respectively. Most preferably the moisture content is from 75 to 85 percent. Controlling the moisture content of the cellulose derivative prior to grinding and partially drying in step B) is essential. If the moisture content prior to step B) is not within the range of 60 to 95 percent, it is adjusted to this range before treating the cellulose derivative in the gas-swept impact mill. The moisture content can be determined by ASTM method D-2363-79 (reapproved 1989). The moisture content can be adjusted by addition of a liquid, for example, water, isopropanol, acetone, methylethylketone or brine. Most preferably, water is used. The amount of liquid added to the water-soluble cellulose derivative should be adjusted to the moisture content that the cellulose derivative already has.

The temperature of the cellulose derivative prior to drying-grinding is preferably controlled and optionally varied or adjusted in a range from 5 to 80° C., more preferably from 7 to 75° C., most preferably from 10 to 60° C. If a liquid such as water is added to the cellulose derivative prior to drying-grinding, the temperature of the cellulose derivative prior to drying-grinding is preferably controlled and optionally varied or adjusted by controlling and optionally varying or adjusting the temperature of the added liquid and/or the jacket temperature of the compounder.

The cellulose derivative having a moisture content of from 60 to 95 percent is usually in the shape of moist granules, moist lumps and/or a moist paste. In step B) it is subjected to grinding and partially drying in a gas-swept impact mill, preferably an air-swept impact mill, wherein the cellulose derivative is subjected to an impacting and/or shearing stress.

Preferred gas-swept impact mills are Ultra Rotor mills (Altenburger Maschinen Jaeckering, Germany) or Turbofiner PLM mills (PALLMANN Maschinenfabrik GmbH & Co. KG, Germany). Gas classifier mills are also useful gas-swept impact mills, for example, the Hosokawa Alpine Air Classifier mill—ZPS Circoplex Hosokawa Micron Ltd., Cheshire, England. Drying is typically accomplished with a combination of hot gas and mechanical energy. Hot air is most commonly used but also hot nitrogen gas can be used. The hot gas and the wet product stream are generally fed via separate inlets into the mill, typically hot gas from the bottom and wet product at a side entrance via a feed screw system connected to the mill Superheated vapor of a solvent, such as superheated steam, or a steam/inert gas mixture or a steam/air mixture can also be used as heat-transfer gas and transport gas, as described in more detail in European Patent Applications EP 0 954 536 A1 (equivalent to U.S. Pat. No. 6,320,043) and EP 1 127 910 A1 (equivalent to U.S. Pat. No. 7,259,257). The circumferential speed of the drying-grinding device is preferably controlled in a range from 35 to 140 m/s, more preferably from 70 to 130 m/s, most preferably from 80 to 120 m/s.

It is an essential feature of the process of the present invention that in step B) of the process the moist cellulose derivative is ground but only partially dried and in step C) of the process the ground and partially dried cellulose derivative is contacted with an additional amount of a drying gas outside the gas-swept impact mill. Preferably the ratio of the gas flow in the gas-swept impact mill in step B) and the flow of the additional amount of drying gas in step C), i.e. (gas flow in step B)/(additional gas flow in step C) is from 1:10 to 8:1, preferably from 1:5 to 3:1, more preferably from 1:3 to 2:1, most preferably from 1:2 to 1:1. The term "additional amount of a drying gas" as used herein means a drying gas that has not been fed into the gas-swept impact mill. The skilled artisan knows how to achieve only a partial drying in step B). E.g., the gas stream can be determined that would be necessary to essentially dry the cellulose derivative in the gas-swept impact mill at the given process parameters, such as gas temperature and moisture content and temperature of the moist cellulose derivative. Incomplete drying can be achieved in step B), e.g., by feeding a lower amount of gas per unit of cellulose derivative to be ground and dried into the gas-swept impact mill than the amount of gas that would be required to dry and grind the cellulose derivative to an essentially dry product in the gas-swept impact mill. In a preferred aspect of the present invention the gas stream used for drying the cellulose derivative is split into two streams via a slide valve wherein the first gas stream is fed into the gas-swept impact mill and the second stream is contacted with the ground and partially dried cellulose derivative that leaves the impact mill. The first gas stream can be partially or fully separated from the ground and partially dried cellulose derivative before the cellulose derivative is contacted with the second gas stream, but preferably the cellulose derivative is suspended in the entire amount or in at least a portion of the gas stream exiting the gas-swept impact mill when it is contacted with the second gas stream. In one aspect of step B) of the process the moist cellulose derivative and a gas are fed into the gas-swept impact mill at a rate of from 52 to 67 m$^3$/kg, more preferably from 55 to 65 m$^3$/kg cellulose derivative, based on the dry weight of cellulose derivative. In one aspect of step C) of the process the ground and partially dried cellulose derivative is contacted with an additional amount of drying gas outside the gas-swept impact mill at a rate of from 25 to 150 m$^3$/kg, more preferably from 50 to 100 m$^3$/kg cellulose derivative, based on the dry weight of cellulose derivative. Preferably hot air or hot nitrogen gas is used. In the drying step C) of the process of the present invention the moisture content of the cellulose derivative is typically reduced to 1 to 20 percent, preferably 1 to 10 percent, more preferably 1 to 5 percent, based on the total weight of the moist cellulose derivative.

After step C) the ground and dried cellulose derivative is preferably subjected to gas classification, typically as described below. The finely divided solid particles are preferably separated from the flow of gas in a separator arranged down-stream the drying-grinding device. The separator is preferably designed to conduct gas classification, such as air classification. It can be a centrifugal separator such as, for example, a cyclone, or a filtering separator such as a sifter. Alternatively, depending on the construction of the gas-swept impact mill, a gas classification may already take place in the gas-swept impact mill. The transport gas may be recycled to the gas-swept impact mill device.

The particulate cellulose derivative that is produced according to the process of the present invention generally has an untapped bulk density of at least 0.40 g/cm$^3$, preferably at least 0.45 g/cm$^3$, and more preferably even at least 0.48 g/cm$^3$. Bulk densities of up to 0.55 g/cm$^3$ are generally achieved, or under optimized conditions even up to 0.60 g/cm$^3$. Bulk density (BD) as used herein is defined as the ratio of apparent volume to mass of the material taken, called untapped bulk density, and also the ratio of tapped volume to mass of material taken, called tapped bulk density. A useful procedure for measuring these bulk densities is described in United States Pharmacopeia 24, Test 616 "Bulk Density and Tapped Density," United States Pharmacopeia Convention, Inc., Rockville, Md., 1999.

Surprisingly, it has been found that the above described process is also useful for increasing the flowability and/or the onset dissolution temperature of particulate cellulose derivatives.

The particulate cellulose derivative that is produced according to the process of the present invention generally has a Carr index of 30 or less, preferably of 28 or less, more preferably of 25 or less. Generally the Carr index is 13 or more, typically 15 or more, more typically 17 or more, and in some cases 20 or more. The Carr index C is an indication of the compressibility of a powder. It is calculated by the formula $$C=100*(BD\text{ tapped}-BD\text{ untapped})/BD\text{ tapped},$$

wherein "BD tapped" is the tapped bulk density of a powder and "BD untapped" is the untapped bulk density of a powder. The Carr index is frequently used in the pharmaceutical science as an indication of the flowability of a powder. A Carr index of greater than 30 is usually an indication of poor flowability of a powder.

The particulate cellulose derivative that is produced according to the process of the present invention generally has an onset dissolution temperature of at least 61.5° C., preferably at least 62.5° C., and more preferably at least 63.0° C. An onset dissolution temperature of up to 67° C. is generally achieved, or under optimized conditions even up to 70° C. The onset dissolution temperature can be determined with a HAAKE RS 1 viscometer (Thermo Scientific, Karlsruhe, Germany) by measuring the viscosity build-up of a product in water. Hereby the temperature of the product mixture is decreased according to a fixed temperature profile of 1° C./min, e.g. starting at 80° C. and ending at 5° C., resulting in a torque build-up curve as function of temperature. A tangent is drawn at the viscosity build-up curve where it shows the steepest slope. The point of intersection of this tangent with the temperature axis is called "onset dissolution temperature". FIG. 1 is a graphical representation how to determine the onset dissolution temperature of a particulate cellulose derivative. In FIG. 1 the onset powder dissolution temperature is 51° C.

Moreover, the process of the present invention is useful for producing cellulose derivatives of a certain size and shape. Particle size and shape of a particulate cellulose derivative can be determined by a high speed image analysis method which combines particle size and shape analysis of sample images. An image analysis method for complex powders is described in: W. Witt, U. Köhler, J. List, Current Limits of Particle Size and Shape Analysis with High Speed Image Analysis, PARTEC 2007. A high speed image analysis system is commercially available from Sympatec GmbH, Clausthal-Zellerfeld, Germany as dynamic image analysis (DIA) system QICPIC™. The high speed image analysis system is useful for measuring among others the following dimensional parameters of particles:

EQPC:

EQPC of a particle is defined as the diameter of a circle that has the same area as the projection area of the particle. For the purpose of the present invention the median EQPC is the volume distribution average of all particles in a given sample of a particulate cellulose derivative. The median EQPC means that 50% of the EQPC of the particle distribution is smaller than the given value in µm and 50% is larger.

LEFI:

The particle length LEFI is defined as the longest direct path that connects the ends of the particle within the contour of the particle. "Direct" means without loops or branches. For the purpose of the present invention the median LEFI is the volume distribution average of all particles in a given sample of a particulate cellulose derivative. The median LEFI means that 50% of the LEFI of the particle distribution is smaller than the given value in µm and 50% is larger.

The particulate cellulose derivative that is produced according to the process of the present invention generally has a median Equivalent Projected Circle Diameter (EQPC) of less than 140 micrometers, preferably of no more than 130 micrometers, more preferably of no more than 125 micrometers and most preferably of no more than 120 micrometers. The particulate cellulose derivative generally has a median EQPC of at least 30 micrometers, preferably at least 35 micrometers, more preferably at least 40 micrometers, and most preferably at least 45 micrometers. WO 2008/127794 discloses a granular material having a mean particle diameter of at least 150 micrometers, using a RapidVue 5× image analyzer which is commercially available from Beckman Coulter, Inc., California. USA; this corresponds to a median EQPC of at least 141 micrometers, measured using the dynamic image analysis (DIA) system QICPIC™.

The particulate cellulose derivative that is produced according to the process of the present invention generally has a median LEFI of from 60 to 350 micrometers, more preferably from 63 to 300 micrometers, most preferably from 65 to 270 micrometers.

The present invention further relates to particulate cellulose derivative having i) a median Equivalent Projected Circle Diameter (EQPC) of less than 140 micrometers, preferably of no more than 130 micrometers, more preferably of no more than 125 micrometers and most preferably of no more than 120 micrometers, and ii) an untapped bulk density of at least 0.40 g/cm$^3$, preferably at least 0.45 g/cm$^3$, and more preferably at least 0.48 g/cm$^3$, and iii) a Carr Index of 30 or less, preferably of 28 or less, and more preferably of 25 or less. The particulate cellulose derivative of the present invention generally has a median EQPC of at least 30 micrometers, preferably at least 35 micrometers, more preferably at least 40 micrometers, and most preferably at least 45 micrometers and/or an untapped bulk density of up to 0.60 g/cm$^3$, typically of up to 0.55 g/cm$^3$ and/or a Carr Index of generally 13 or more, typically 15 or more, more typically 17 or more, and in some cases 20 or more.

The particulate cellulose derivative that is produced according to the process of the present invention and the novel particulate cellulose derivative of the present invention is useful in a variety of applications, for example in pharmaceutical applications, preferably in liquid suspensions comprising a cellulose derivative and a medicament, or solutions of the particulate cellulose derivative for the preparation of hard shell capsules.

Among other uses, the cellulose derivative is useful as an excipient for a dosage form, particularly as an excipient for a sustained-release dosage form, which means that it has the function to regulate the release of an active ingredient from the dosage form over an extended period of time. The term "sustained-release" is used herein synonymously to the terms prolonged release; extended release; sustained release; depot release; time release; controlled release; modified release or prolonged action. "Sustained release" is an approach by which active compounds, such as biologically active compounds, are made available at a rate and duration designed to accomplish an intended effect. For example, an oral controlled release drug delivery system is a device or dosage form that regulates the release of a drug into the gastrointestinal tract, thereby controlling the absorption rate of that drug in order to achieve a desired blood plasma profile. These dosage forms are designed to provide a constant or nearly constant drug level in plasma with reduced fluctuation via a slow, continuous release of drug over an extended period of time. In the sustained-release dosage form of the present invention it generally takes between 0.75 and 36 hours, more preferably between 4 and 30 hours, and most preferably between 8 and 24 hours to release the active ingredient from the dosage form in its entirety.

The above-described cellulose derivatives are useful as an excipient for dosage forms, particularly for sustained-release dosage forms in a variety of technological fields, for example in personal care, laundry care or agricultural applications, water treatment, and particularly in human or animal health care applications, most specifically pharmaceutical applications wherein a biologically active ingredient is selected from vitamins, herbal and mineral supplements and drug substances.

The above-described cellulose derivatives have a unique combination of features which makes them very useful as an excipient in dosage forms, for example in pharmaceutical dosage forms. The cellulose derivatives have good flow properties. They can be efficiently blended with a biologically active ingredient, and, if desired, with one or more optional adjuvants, even in the absence of a substantial amount of added solvent or heat. It is to be understood that one or more types of the above-described cellulose derivatives and one or more types of active ingredients can be blended with one or more optional adjuvants to prepare a dosage form. Preferably the blending process is conducted at about room temperature.

A large variety of active ingredients are useful, dependent on the intended end-use of the dosage form. Active ingredients are known in the art and include, among others, detergents or surfactants for laundry care applications; fertilizers, herbicides or pesticides in formulations designed to release the bioactive agents over a prolonged period of time in agricultural applications. A wide range of biologically active ingredients are useful, such as vitamins, herbals and mineral supplements and drugs. The biologically active ingredient includes hydrophobic, hydrophilic and amphiphilic compounds. The biologically active ingredient may be used for treating indications such as, by way of example and without limitation, inflammation, gout, hypercholesterolemia, microbial infection, AIDS, tuberculosis, fungal infection, amoebic infection, parasitic infection, cancer, organ rejection, diabetes, heart failure, arthritis, asthma, pain, congestion, urinary tract infections, vaginal infection, seizure-related disorders, depression, psychosis, convulsion, diabetes, blood coagulation, hypertension and birth control. The amount of the biologically active ingredient loaded into a pharmaceutical dosage form will vary according to the pharmacological activity of the compound, the indication being treated, the targeted dosing regimen, the projected method of administration, the integrity or stability of the final composition or other such reasons.

The amount of the active ingredient generally is at least 0.5 percent, preferably at least 1 percent, more preferably at least 5 percent, most preferably at least 10 percent, based on the total weight of the dosage form, and generally up to 75 percent, preferably up to 65 percent, more preferably up to 55 percent, most preferably up to 45 percent, based on the total weight of the dosage form. The active ingredient is generally solid and preferably has a median particle diameter of from 1 to 500 micrometers. Useful optional adjuvants are known in the art and are generally solid, such as one or more fillers, pigments, colorants, flavorants, disintegrating agents, binders, plasticizers, salts, acidic and basic pH modifiers, antioxidants and/or lubricants. Examples of such adjuvants are acacia, corn starch, guar gum, potato starch, alginic acid, stearic acid, magnesium stearate, lactose, sucrose, dicalcium phosphate, microcrystalline cellulose, sugars, minerals, cellulose powder or cellulose fibers. Optional adjuvants are generally solid and preferably have a median particle diameter of from 1 to 500 micrometers.

The present invention is further illustrated by the following Examples which are not to be construed to limit the scope of the invention. Unless otherwise indicated, all parts and percentages are by weight.

Examples 1-2 and Comparative Examples A-F

A commercially available continuous compounder with heating and cooling jacket was used to add water to dry METHOCEL™ K100M cellulose ether. The compounder jacket was supplied with a fluid of −16° C. to 73° C. The fluid in the compounder jacket is used to adapt the temperature of the cellulose ether prior to drying-grinding, but the temperature of the cellulose ether is measured separately and usually does not reach the temperature of the fluid in the compounder jacket because the water mixed with the cellulose ether in the compounder is only between 2 and 11 deg C.

The cellulose ether of Examples 1-2 and Comparative Examples A-F was produced as the commercially available material METHOCEL™ K100M cellulose ether which is commercially available from The Dow Chemical Company, but it was used in Examples 1-2 and Comparative Examples A-F without having been ground after production. METHOCEL™ K100M cellulose ether has a degree of substitution of methoxyl groups of 22.0-24.0% and of hydroxypropyl groups of 9.5-11.5%, and a viscosity of 75,000-140,000 mPa·s, measured as a 2 percent aqueous solution at 20° C. METHOCEL™ K100M used as feedstock in the compounder for Examples 1-2 and Comparative Examples A-F had an onset dissolution temperature of 53° C.

METHOCEL™ K100M having a moisture content of less than 5%, based on the total weight of the moist cellulose ether, was fed continuously at a feed rate of 30 kg/h into the compounder. Water of a temperature of 2° C. to 11° C. was continuously added at rates of 30-120.3 kg/h to the compounder resulting in a moisture level of about 49.1 to 81.8%. The wet product was transported continuously via a transport belt into a mill feed unit (Altenburger Maschinen Jaeckering GmbH, Hamm, Germany). The bottom blades of the vessel agitator pressed the paste into a single augur screw mounted at the bottom of the vessel. The wet product was forced through a perforated plate directly into the side of an Ultrarotor II "S" impact mill (Altenburger Maschinen Jaeckering GmbH, Hamm, Germany) between the first and second grinding stage. The mill was equipped with seven grinding stages. The bottom three grinding stages were equipped with standard grinding bars. Turbo-bars were installed in the top four grinding stages. A co-rotating finger sifter wheel with twelve blades was installed on the top of the 7th grinding stage. The interior of mill jacket had the standard Altenburger corrugated stationary grinding plates.

The rotor of the impact mill was operated at a circumferential speed of 114 m/s. A total hot gas stream of 1362 to 1437 $m^3/h$ was generated via a natural gas burner. For Examples 1 and 2 and Comparative Examples D and F the total gas stream was split into two streams. The primary stream was operated into the bottom of the mill; the secondary stream was combined with the primary stream after the latter had left the mill enabling flash drying of the milled product. The primary hot gas stream, i.e. nitrogen was fed at a rate of 585 $m^3/h$ to 1437 $m^3/h$ into the bottom of the mill. The secondary hot gas stream results from the difference between the total gas stream and the primary hot gas stream, i.e. nitrogen. A cyclone was used to separate the dried product from the nitrogen. The final product moisture was smaller than 1.3-2.9% by weight.

Comparative Example G (CR)

Hydroxypropyl methylcellulose having a degree of substitution of methoxyl groups of 22.6% and of hydroxypropoxyl groups of 10.3%, and a viscosity of 114,700 Pa·s, is used as a comparative material. It is representative of state of the art controlled release grade cellulose ether and referred to as CR cellulose ether. The production of controlled release grade cellulose ethers is disclosed in U.S. Pat. No. 4,734,285.

Comparative Example H (DC)

Hydroxypropl methylcellulose having a degree of substitution of methoxyl groups of 22.7% and of hydroxypropoxyl groups of 10.0%, and a viscosity of 103,300 mPa·s, is used as a comparative material. The hydroxypropyl methylcellulose of Comparative Example H can be produced by a granulation process as described in WO 2008/127794. The hydroxypropyl methylcellulose of Comparative Example H is referred to as "Direct Compression" (DC) cellulose ether.

Determination of Properties

The onset dissolution temperature of the cellulose derivative was determined with a HAAKE RS 1 viscometer by measuring the viscosity build-up of a product in water, as described in more detail further above.

The tapped and untapped bulk density of the cellulose derivative in particulate form was measured using a Hosokawa Powder Characteristics Tester: Model PT-N available from Hosokawa Micron, Osaka Japan.

The median LEFI and the median EQPC are the volume distribution average of the LEFIs and EQPCs of all particles in a given sample of a particulate cellulose derivative, which were measured by an image analyzer (high speed image analyzer sensor QICPIC, Sympatec, Germany, with dry disperser RODOS/L with an inner diameter of 4 mm and dry feeder VIBRI/L and Software WINDOX5, Vers. 5.3.0 and M7 lens)

The conditions of the process of the present invention and the properties of the produced particulate cellulose derivatives are listed in Table 1 below.

In all Examples and Comparative Examples the cellulose derivatives are cellulose ethers (CE).

C) contacting the ground and partially dried cellulose derivative with a second drying gas stream outside the gas-swept impact mill, wherein the cellulose derivative is suspended in the entire amount or in at least a portion of the first drying gas stream exiting the gas swept impact mill when the cellulose derivative is contacted with the second drying gas stream outside the gas-swept impact mill to produce the particulate cellulose derivative.

TABLE 1

| (Comparative) Example | CE Moisture [%]* | CE Temperature [° C.]* | Water Temperature [° C.] | Total Gas Flow [m³/h] | Gas Flow Mill [m³/h] | Through-put solid CE [kg/h] | Gas/Solids in mill [m³/kg] | Gas/Solids in Gas dryer [m³/kg] | Onset Dissolution Temp. [° C.] | Median LEFI [μm] | Median EQPC [μm] | BD untapped [g/l] | BD tapped [g/l] | Carr Index |
|---|---|---|---|---|---|---|---|---|---|---|---|---|---|---|
| A | 80.0 | 20.5 | 11.0 | 1376 | 1376 | 20.0 | 68.8 | — | 60.3 | 171 | 73 | 316 | 467 | 32.3 |
| 1 | 80.4 | 20.4 | 11.0 | 1362 | 565 | 9.2 | 61.4 | 86.6 | 64.5 | 83 | 52 | 495 | 645 | 23.3 |
| B | 81.8 | 58.3 | 10.6 | 1405 | 1405 | 13.0 | 108.0 | — | 60.7 | 187 | 81 | 323 | 467 | 30.8 |
| 2 | 80.7 | 58.8 | 10.5 | 1422 | 609 | 10.1 | 60.3 | 80.5 | 63.3 | 129 | 58 | 505 | 654 | 22.8 |
| C | 49.5 | 27.1 | 2.0 | 1404 | 1404 | 33.6 | 41.8 | — | 55.3 | 362 | 99 | 182 | 313 | 41.9 |
| D | 49.1 | 26.4 | 3.0 | 1422 | 647 | 16.2 | 39.9 | 47.8 | 55.4 | 343 | 79 | 222 | 408 | 45.6 |
| E | 49.9 | 58.3 | 5.1 | 1437 | 1437 | 31.8 | 45.2 | — | 55.2 | 463 | 103 | 210 | 353 | 40.5 |
| F | 49.8 | 57.5 | 4.6 | 1394 | 585 | 13.6 | 43.0 | 59.5 | 55.4 | 417 | 94 | 232 | 406 | 42.9 |
| G (CR) | — | — | — | — | — | — | — | — | — | 265 | 93 | 302 | | |
| H (DC) | — | — | — | — | — | — | — | — | — | 395 | 153 | 164 | | |

*prior to drying and grinding

Table 1 illustrates the improved flowability, and the higher bulk density of the cellulose derivatives of the present invention, as compared to the known cellulose derivatives of comparative Examples G and H.

Table 1 also illustrates the improved flowability (a lower Carr index), a higher bulk density and a higher onset dissolution temperature that are achieved when the cellulose derivatives are produced according to the process of the present invention, i.e., when the moisture content of the cellulose derivative is adjusted to 60 to 95 percent, based on the total weight of the moist cellulose derivative, prior to the grinding and drying step (Compare Examples 1 and 2 with Comparative Examples D and F) and when the moist cellulose derivative is ground but only partially dried in a gas-swept impact mill and contacted with an additional amount of drying gas outside the gas-swept impact mill (Compare Examples 1 and 2 with Comparative Examples A and B). However, when the moisture content of the cellulose derivative is substantially below 60 percent, the flowability is not much improved (the Carr index is not much decreased) and the onset dissolution temperature is not significantly increased when the moist cellulose derivative is ground but only partially dried in a gas-swept impact mill and contacted with an additional amount of drying gas outside the gas-swept impact mill (Compare Comparative Examples D and F with Comparative Examples C and E). Comparative Examples A to F are not prior art.

What is claimed is:

1. A process for producing a particulate cellulose derivative by grinding and drying a moist cellulose derivative using a drying gas stream, comprising the steps of
   A) providing a moist cellulose derivative having a moisture content of from 60 to 95 percent, based on the total weight of the moist cellulose derivative,
   B) grinding and partially drying the moist cellulose derivative in a gas-swept impact mill into which a first drying gas stream is fed; and 2. The process of claim 1 wherein the moisture content of the moist cellulose derivative in step A), prior to grinding and drying, is from 75 to 85 percent, based on the total weight of the moist cellulose derivative.

3. The process of claim 1 wherein the ratio of the gas flow of first drying gas stream in the gas-swept impact mill in step B) and the flow of the second drying gas stream in step C) is from 1:10 to 8:1.

4. The process of claim 1 wherein
   in step B) moist cellulose derivative and the first drying gas stream are fed into the gas-swept impact mill at a rate of from 52 to 67 m³ drying gas/kg cellulose derivative, based on the dry weight of cellulose derivative, and/or
   in step C) a second drying gas stream is contacted with the cellulose derivative at an amount of from 25 to 150 m³ drying gas/kg cellulose derivative, based on the dry weight of cellulose derivative.

5. The process of claim 1 wherein the cellulose derivative is a cellulose ether.

6. The process of claim 1 wherein the produced particulate cellulose derivative has a median Equivalent Projected Circle Diameter (EQPC) of less than 140 micrometers.

7. The process of claim 1 wherein the produced particulate cellulose derivative has an untapped bulk density of at least 0.40 g/cm³.

8. The process of claim 1 wherein the produced particulate cellulose derivative has a Carr Index of 30.0 or less.

9. The process of claim 1 wherein the produced particulate cellulose derivative has an onset dissolution temperature of at least 61.5° C.

10. A method of increasing the flowability and/or the onset dissolution temperature of a particulate cellulose derivative comprising the steps of
   A) providing a moist cellulose derivative having a moisture content of from 60 to 95 percent, based on the total weight of the moist cellulose derivative,
   grinding and partially drying the moist cellulose derivative in a gas-swept impact mill into which a first drying gas stream is fed; and contacting the ground and partially dried cellulose derivative with a second drying gas stream outside the gas-swept impact mill, wherein the cellulose derivative is suspended in the entire amount or in at least a portion of the first drying gas stream exiting the gas swept impact mill when the suspended cellulose derivative is contacted with the second gas stream outside the gas-swept impact mill.

11. The process of claim 1 wherein the drying gas stream used for drying the cellulose derivative is split into two drying gas streams via a slide valve wherein the first drying gas stream is fed into the gas-swept impact mill and the second drying gas stream is contacted with the ground and partially dried cellulose derivative that leaves the impact mill such that the cellulose derivative is suspended in the entire amount or in at least a portion of the drying gas stream exiting the gas swept impact mill when the cellulose derivative is contacted with the second drying gas stream.

* * * * *